US008306622B2

(12) United States Patent
Arcot-Krishnamurthy et al.

(10) Patent No.: US 8,306,622 B2
(45) Date of Patent: Nov. 6, 2012

(54) LEFT ATRIAL SENSE OR CAPTURE DETECTION FROM CORONARY SINUS

(75) Inventors: Shantha Arcot-Krishnamurthy, Vadnais Heights, MN (US); Shibaji Shome, Minneapolis, MN (US); Yanting Dong, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 224 days.

(21) Appl. No.: 12/892,378

(22) Filed: Sep. 28, 2010

(65) Prior Publication Data

US 2011/0098768 A1    Apr. 28, 2011

Related U.S. Application Data

(60) Provisional application No. 61/255,744, filed on Oct. 28, 2009.

(51) Int. Cl.
*A61N 1/00* (2006.01)

(52) U.S. Cl. .......................................................... 607/28

(58) Field of Classification Search .................. 607/4–28
See application file for complete search history.

(56) References Cited

U.S. PATENT DOCUMENTS

| | | | |
|---|---|---|---|
| 6,640,136 | B1 | 10/2003 | Helland et al. |
| 6,697,673 | B1 | 2/2004 | Lu |
| 6,885,893 | B1 | 4/2005 | Lu |
| 7,139,610 | B2 | 11/2006 | Ferek-Petric |
| 7,203,543 | B2 | 4/2007 | Meyer et al. |
| 7,567,836 | B2 | 7/2009 | Zhang |
| 7,583,998 | B2 | 9/2009 | Meyer et al. |
| 7,613,514 | B2 | 11/2009 | Fogoros et al. |
| 2005/0149137 | A1 | 7/2005 | Chinchoy et al. |
| 2007/0066998 | A1 | 3/2007 | Hansen et al. |
| 2009/0043351 | A1 | 2/2009 | Sathaye et al. |
| 2009/0216291 | A1 | 8/2009 | Holmstrom et al. |
| 2010/0010557 | A1 | 1/2010 | Fogoros et al. |

*Primary Examiner* — Scott Getzow

(74) *Attorney, Agent, or Firm* — Schwegman Lundberg & Woessner, P.A.

(57) ABSTRACT

A method and device to detect and compare changes in atrial rate and morphology can be used to identify left atrial sense and capture, such as from a quadripolar or other lead located in or around the coronary sinus.

20 Claims, 6 Drawing Sheets

LEFT ATRIAL SENSE OR CAPTURE DETECTION FROM CORONARY SINUS

CROSS-REFERENCE TO RELATED APPLICATION

This application claims the benefit of U.S. Provisional Application No. 61/255,744, filed on Oct. 28, 2009, under 35 U.S.C. §119(e), which is incorporated herein by reference in its entirety.

BACKGROUND

The coronary sinus is a collection of veins joined together to form a large vessel that collects blood from the myocardium. The coronary sinus runs transversely in the groove between the left atrium and left ventricle on the posterior surface of the heart, and it empties into the right atrium. Leads designed for placement in the coronary sinus can include electrodes that can be positioned in the atrioventricular (AV) groove region between the left atrium and left ventricle or in association with the left ventricle, for example.

OVERVIEW

The present inventors have recognized, among other things, that the exact location of the electrodes of a lead placed in the coronary sinus region can be dictated by the venous anatomy (e.g., vein diameters) of a subject's heart. In some cases, the electrodes can be located near the AV groove, and in other cases they can be located in the left ventricular area. Depending on their location, these electrodes may detect electrical heart signals from either the left atrium or the left ventricle. Thus, determining the location of the electrodes, as well as which cardiac chamber the electrodes are sensing or capturing, can be important for a variety of purposes, including administering cardiac resynchronization therapy, monitoring atrial remodeling, or detecting interatrial conduction abnormalities, for example.

Example 1 can include subject matter that can include a pacing circuit comprising a coronary sinus pacing electrode configured to be inserted via a coronary sinus of a heart of a subject, the coronary sinus pacing electrode configured to pace a first atrial chamber; a sensing circuit configured to sense an atrial depolarization associated with a different second atrial chamber; a measurement circuit, coupled to the pacing circuit and the sensing circuit, the measurement circuit configured to: perform a first measurement of a parameter of the second atrial chamber depolarization in the absence of pacing from the coronary sinus pacing electrode, wherein the second atrial chamber depolarization is sensed in the absence of pacing from the coronary sinus pacing electrode; and perform a second measurement of the same parameter of the second atrial chamber depolarization in the presence of pacing from the coronary sinus pacing electrode, wherein the second atrial chamber depolarization is sensed in the presence of pacing from the coronary sinus pacing electrode; and a controller circuit, coupled to the measurement circuit, the controller circuit configured to compare a change between the first and second measurements to a criterion, and when the change meets the criterion, to declare that the first atrial chamber has been captured by the pacing from the coronary sinus pacing electrode.

In Example 2, the subject matter of Example 1 can optionally include the change between the first and second measurements comprising an increase in heart rate.

In Example 3, the subject matter of any one of Examples 1-2 can optionally include the change between the first and second measurements comprising a change in a cardiac depolarization morphology characteristic.

In Example 4, the subject matter of any one of Example 1-3 can optionally include the change between the first and second measurements comprising a change in at least one of: a P-wave duration, a P-wave vector direction, a P-wave amplitude, a P-wave slope, a P-wave power, or a P-wave frequency content, a P-wave area, a P-wave morphological feature, a P-wave spatiotemporal characteristic, or a change in depolarization conduction time between the coronary sinus pacing electrode and an electrode associated with the second atrial chamber.

In Example 5, the subject matter of any one of Examples 1-4 can optionally include the controller circuit being coupled to the pacing circuit and configured to vary an energy of paces delivered by the coronary sinus pacing electrode to determine a first atrial chamber capture threshold energy associated with the coronary sinus pacing electrode.

In Example 6, the subject matter of any one of Examples 1-5 can optionally include the change between the first and second measurements comprising a change in heart rate and a change in a depolarization morphology characteristic.

In Example 7, the subject matter of any one of Examples 1-6 can optionally include a coronary sinus sensing electrode, configured to be inserted via a coronary sinus of the heart of the subject, the coronary sinus sensing electrode configured to sense a cardiac depolarization; wherein the measurement circuit is configured to measure a delay between the sensed second atrial chamber depolarization and the sensed cardiac depolarization sensed at the coronary sinus sensing electrode during the same cardiac cycle; and wherein the controller circuit is configured to use information about the delay to determine whether the sensed cardiac depolarization is associated with the first atrial chamber.

In Example 8, the subject matter of any one of Examples 1-7 can optionally include the coronary sinus sensing electrode and the coronary sinus pacing electrode being the same electrode.

In Example 9, the subject matter of any one of Examples 1-8 can optionally include the controller circuit configured to compare the delay to a specified threshold value, and when the delay is less than the specified threshold value, to declare that the sensed cardiac depolarization is associated with the first atrial chamber.

In Example 10, the subject matter of any one of Examples 1-9 can optionally include the coronary sinus sensing electrode comprising first and second coronary sinus sensing electrodes located at different coronary sinus locations; wherein the measurement circuit is configured to: measure a first delay between the sensed second atrial chamber depolarization and the sensed cardiac depolarization sensed at the first coronary sinus sensing electrode during the same cardiac cycle; and measure a second delay between the sensed second atrial chamber depolarization and the sensed cardiac depolarization sensed at the second coronary sinus sensing electrode during the same cardiac cycle; and wherein the controller is configured to compare a change in the first delay relative to the second delay to determine whether the sensed cardiac depolarization is associated with the first atrial chamber.

Example 11 can include, or can optionally be combined with any one of Examples 1-10 to include subject matter that can include: designating a first atrial chamber for pacing from a coronary sinus pacing electrode that has been inserted via a coronary sinus of a heart of a subject; designating a different second atrial chamber for sensing an atrial depolarization associated with the second atrial chamber; sensing a second atrial chamber depolarization in the absence of pacing from the coronary sinus pacing electrode, and performing a first measurement of a parameter of the second atrial chamber depolarization in the absence of pacing from the coronary sinus pacing electrode; sensing the second atrial chamber depolarization in the presence of pacing from the coronary sinus pacing electrode, and performing a second measurement of the same parameter of the second atrial chamber depolarization in the presence of pacing from the coronary sinus pacing electrode; and comparing a change between the first and second measurements to a criterion, and when the change meets the criterion, declaring that the first atrial chamber has been captured by the pacing from the coronary sinus pacing electrode.

In Example 12, the subject matter of any one of Examples 1-11 can optionally include the change between the first and second measurements comprising an increase in heart rate.

In Example 13, the subject matter of any one of Examples 1-12 can optionally include the change between the first and second measurements comprising a change in a cardiac depolarization morphology characteristic.

In Example 14, the subject matter of any one of Examples 1-13 can optionally include the change between the first and second measurements comprising a change in at least one of: a P-wave duration, a P-wave vector direction, a P-wave amplitude, a P-wave slope, a P-wave power, a P-wave frequency content, a P-wave area, a P-wave morphological feature, a P-wave spatiotemporal characteristic, or a change in depolarization conduction time between the coronary sinus pacing electrode and an electrode associated with the second atrial chamber.

In Example 15, the subject matter of any one of Examples 1-14 can optionally include varying an energy of paces delivered by the coronary sinus pacing electrode to determine a first atrial chamber capture threshold energy associated with the coronary sinus pacing electrode.

In Example 16, the subject matter of any one of Examples 11-15 can optionally include the change between the first and second measurements comprising a change in heart rate and a change in a depolarization morphology characteristic.

In Example 17, the subject matter of any one of Examples 11-16 can optionally include sensing a cardiac depolarization using a coronary sinus sensing electrode that has been inserted via a coronary sinus of the heart of the subject; measuring a delay between the sensed second atrial chamber depolarization and the sensed cardiac depolarization sensed at the coronary sinus sensing electrode during the same cardiac cycle; and using information about the delay to determine whether the sensed cardiac depolarization is associated with the first atrial chamber.

In Example 18, the subject matter of any one of Examples 1-17 can optionally include the coronary sinus sensing electrode and the coronary sinus pacing electrode being the same electrode.

In Example 19, the subject matter of any one of Examples 1-18 can optionally include comparing the delay to a specified threshold value, and when the delay is less than the specified threshold value, declaring that the sensed cardiac depolarization is associated with the first atrial chamber.

In Example 20, the subject matter of any one of Examples 1-19 can optionally include sensing a cardiac depolarization using first and second coronary sinus sensing electrodes located at different coronary sinus locations; wherein measuring a delay includes: measuring a first delay between the sensed second atrial chamber depolarization and the sensed cardiac depolarization sensed at the first coronary sinus sensing electrode during the same cardiac cycle; and measuring a second delay between the sensed second atrial chamber depolarization and the sensed cardiac depolarization sensed at the second coronary sinus sensing electrode during the same cardiac cycle; and wherein using information about the delay includes comparing a change in the first delay relative to the second delay to determine whether the sensed cardiac depolarization is associated with the first atrial chamber.

Example 1A can include subject matter that can include a coronary sinus sensing electrode, configured to be inserted via a coronary sinus of a heart of a subject, the coronary sinus sensing electrode configured to sense a cardiac depolarization; an atrial chamber electrode associated with an atrial chamber of the heart of the subject, the atrial chamber electrode configured to sense an atrial depolarization; a measurement circuit, coupled to the coronary sinus sensing electrode and the atrial chamber electrode, the measurement circuit configured to measure a delay between the sensed atrial depolarization and the sensed cardiac depolarization sensed at the coronary sinus sensing electrode during the same cardiac cycle; and a controller circuit, coupled to the measurement circuit, the controller circuit configured to use information about the delay to determine the sensed cardiac depolarization is associated with an atrial chamber.

In Example 2A, the subject matter of Example 1A can optionally include the controller circuit configured to compare the delay to a specified threshold value, and when the delay is less than the specified threshold value, to declare that the sensed cardiac depolarization is associated with an atrial chamber.

In Example 3A, the subject matter of any one of Examples 1A-2A can optionally include the coronary sinus sensing electrode comprising first and second coronary sinus sensing electrodes located at different coronary sinus locations; wherein the measurement circuit is configured to: measure a first delay between the sensed atrial depolarization and the sensed cardiac depolarization sensed at the first coronary sinus sensing electrode during the same cardiac cycle; and measure a second delay between the sensed atrial depolarization and the sensed cardiac depolarization sensed at the second coronary sinus sensing electrode during the same cardiac cycle; and wherein the controller is configured to compare a change in the first delay relative to the second delay to determine whether the sensed cardiac depolarization is associated with an atrial chamber.

In Example 4A, the subject matter of any one of Examples 1A-3A can optionally include a coronary sinus pacing electrode configured to be inserted via a coronary sinus of the heart of the subject, the coronary sinus pacing electrode configured to pace a first atrial chamber; wherein the atrial chamber electrode is configured to sense an atrial depolarization associated with a different second atrial chamber; wherein the measurement circuit is configured to: perform a first measurement of a parameter of the second atrial chamber depolarization in the absence of pacing from the coronary sinus pacing electrode, wherein the second atrial chamber depolarization is sensed in the absence of pacing from the coronary sinus pacing electrode; and perform a second measurement of the same parameter of the second atrial chamber depolarization in the presence of pacing from the coronary sinus pacing electrode, wherein the second atrial chamber depolarization is sensed in the presence of pacing from the coronary sinus pacing electrode; and wherein the controller circuit is configured to compare a change between the first and second measurements to a criterion, and when the change meets the criterion, to declare that the first atrial chamber has been captured by the pacing from the coronary sinus pacing electrode.

In Example 5A, the subject matter of any one of Examples 1A-4A can optionally include the coronary sinus sensing electrode and the coronary sinus pacing electrode being the same electrode.

In Example 6A, the subject matter of any one of Examples 1A-5A can optionally include the change between the first and second measurements comprising an increase in heart rate.

In Example 7A, the subject matter of any one of Examples 1A-6A can optionally include the change between the first and second measurements comprising a change in a cardiac depolarization morphology characteristic.

In Example 8A, the subject matter of any one of Examples 1A-7A can optionally include the change between the first and second measurements comprising a change in at least one of: a P-wave duration, a P-wave vector direction, a P-wave amplitude, a P-wave slope, a P-wave power, a P-wave frequency content, a P-wave area, a P-wave morphological feature, a P-wave spatiotemporal characteristic, or a change in depolarization conduction time between the coronary sinus pacing electrode and an electrode associated with the second atrial chamber.

In Example 9A, the subject matter of any one of Examples 1A-8A can optionally include the controller circuit being coupled to the pacing circuit and configured to vary an energy of paces delivered by the coronary sinus pacing electrode to determine a first atrial chamber capture threshold energy associated with the coronary sinus pacing electrode.

In Example 10A, the subject matter of any one of Examples 1A-9A can optionally include the change between the first and second measurements comprising a change in heart rate and a change in a depolarization morphology characteristic.

Example 11A can include, or can optionally be combined with any one of Examples 1A-10A to include subject matter that can include: sensing a cardiac depolarization using a coronary sinus sensing electrode that has been inserted via a coronary sinus of a heart of a subject; sensing or pacing an atrial depolarization using an atrial chamber electrode associated with an atrial chamber of the heart of the subject; measuring a delay between the sensed atrial depolarization and the sensed cardiac depolarization sensed at the coronary sinus sensing electrode during the same cardiac cycle; and using information about the delay to determine the sensed cardiac depolarization is associated with an atrial chamber.

In Example 12A, the subject matter of any one of Examples 1A-11A can optionally include comparing the delay to a specified threshold value, and when the delay is less than the specified threshold value, declaring that the sensed cardiac depolarization is associated with an atrial chamber.

In Example 13A, the subject matter of any one of Examples 1A-12A can optionally include sensing a cardiac depolarization using first and second coronary sinus sensing electrodes located at different coronary sinus locations; wherein measuring a delay includes: measuring a first delay between the sensed atrial depolarization and the sensed cardiac depolarization sensed at the first coronary sinus sensing electrode during the same cardiac cycle; and measuring a second delay between the sensed atrial depolarization and the sensed cardiac depolarization sensed at the second coronary sinus sensing electrode during the same cardiac cycle; and wherein using information about the delay includes comparing a change in the first delay relative to the second delay to determine whether the sensed cardiac depolarization is associated with an atrial chamber.

In Example 14A, the subject matter of subject matter of any one of Examples 1A-13A can optionally include designating a first atrial chamber for pacing from a coronary sinus pacing electrode that has been inserted via a coronary sinus of a heart of a subject; designating a different second atrial chamber for sensing an atrial depolarization associated with the second atrial chamber; sensing a second atrial chamber depolarization in the absence of pacing from the coronary sinus pacing electrode, and performing a first measurement of a parameter of the second atrial chamber depolarization in the absence of pacing from the coronary sinus pacing electrode; sensing the second atrial chamber depolarization in the presence of pacing from the coronary sinus pacing electrode, and performing a second measurement of the same parameter of the second atrial chamber depolarization in the presence of pacing from the coronary sinus pacing electrode; and comparing a change between the first and second measurements to a criterion, and when the change meets the criterion, declaring that the first atrial chamber has been captured by the pacing from the coronary sinus pacing electrode.

In Example 15A, the subject matter of any one of Examples 1A-14A can optionally include the coronary sinus sensing electrode and the coronary sinus pacing electrode being the same electrode.

In Example 16A, the subject matter of any one of Examples 1A-15A can optionally include the change between the first and second measurements comprising an increase in heart rate.

In Example 17A, the subject matter of any one of Examples 1A-16A can optionally include the change between the first and second measurements comprising a change in a cardiac depolarization morphology characteristic.

In Example 18A, the subject matter of any one of Examples 1A-17A can optionally include the change between the first and second measurements comprising a change in at least one of: a P-wave duration, a P-wave vector direction, a P-wave amplitude, a P-wave slope, a P-wave power, a P-wave frequency content, a P-wave area, a P-wave morphological feature, a P-wave spatiotemporal characteristic, or a change in depolarization conduction time between the coronary sinus pacing electrode and an electrode associated with the second atrial chamber.

In Example 19A, the subject matter of any one of Examples 1A-18A can optionally include varying an energy of paces delivered by the coronary sinus pacing electrode to determine a first atrial chamber capture threshold energy associated with the coronary sinus pacing electrode.

In Example 20A, the subject matter of any one of Examples 1A-19A can optionally include the change between the first and second measurements comprising a change in heart rate and a change in a depolarization morphology characteristic.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a device and method for using a coronary sinus lead, such as a quadripolar (four-electrode) lead, such as to identify when an atrial chamber of the heart has been sensed or when an atrial chamber of the heart has been captured.

The present inventors have recognized, among other things that the particular cardiac chamber from which a coronary sinus electrode detects intrinsic electrical heart signals (e.g., depolarizations) can be identified such as by detecting and evaluating a change in atrial rate, atrial morphology, or interatrial delay, such as further described below.

Figure 1:
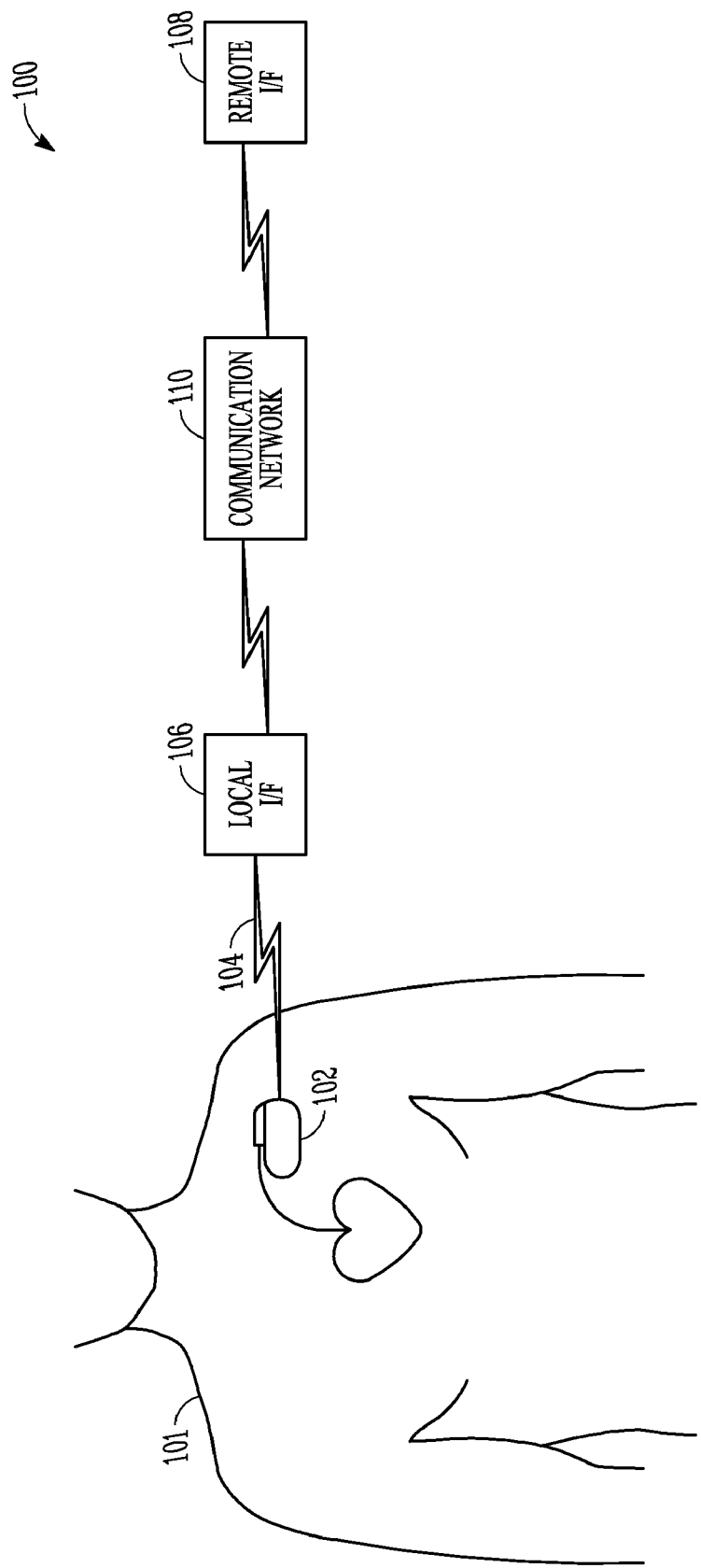
FIG. 1 is schematic diagram illustrating generally an example of a cardiac function management system, such as for use with a human or animal subject.

FIG. 1 is schematic diagram illustrating generally an example of a cardiac function management system 100, such as for use with a human or other living subject 101. In this example, the system 100 can include an implantable or external cardiac function management (CFM) device 102. Examples of CFM device 102 can include, without limitation, a pacemaker, a cardioverter, a defibrillator, a CRT device, or other cardiac monitoring or therapy delivery device, for example, including a cardiac device that includes or works in coordination with one or more neuro-stimulating devices, or other devices, drugs, drug delivery systems, or other therapies. The CFM device 102 can include a communication circuit, such as for establishing a unidirectional or bidirectional wireless communication link 104 with an external local interface 106, with an implantable or external therapy circuit, or with another device with communication capability. In an example, the external local interface 106 can further unidirectionally or bidirectionally communicate with an external remote interface 108, such as wirelessly or otherwise, such as via a shared communication or computer network 110.

Figure 2:
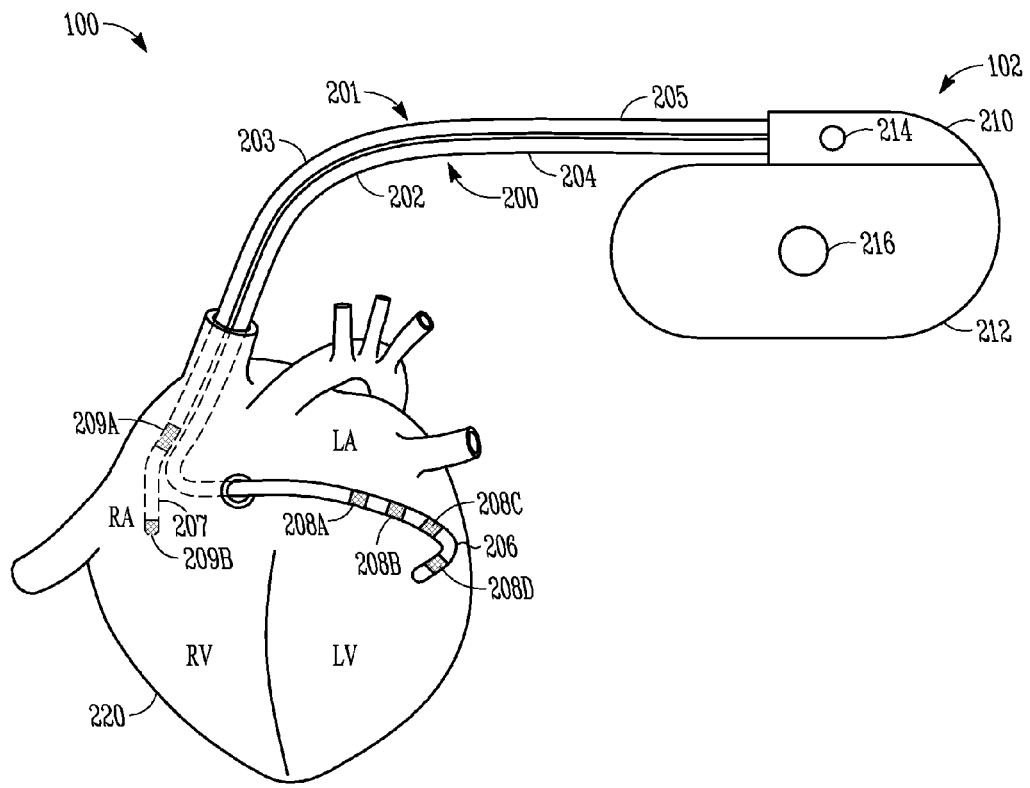
FIG. 2 is a schematic view illustrating generally an example of a quadripolar lead located in the coronary sinus region of the heart.

FIG. 2 is a schematic view illustrating generally an example of a quadripolar coronary sinus lead 200 located in the coronary sinus region of the heart. As shown, the coronary sinus lead 200 includes a lead body 202 extending from a lead proximal end portion 204, where it is couplable with the CFM device 102, to a lead distal end portion 206, which is positionable within or near the coronary sinus region of the heart 220 when fully implanted. In this example, the lead distal end portion 206 includes four electrodes 208A, 208B, 208C, 208D, that electrically link the coronary sinus lead 200 with the heart 220. Although coronary sinus lead 200 is a quadripolar lead in the example shown, it can be a multipolar lead, including two, three, or five or more electrodes, for example. Also shown in FIG. 2 is a right atrial lead 201, which includes a lead body 203 extending from a lead proximal end portion 205, where it is couplable with the CFM device 102, to a lead distal end portion 207, which is positionable within or near the right atrium of the heart 220 when fully implanted. In this example, the lead distal end portion 207 includes two electrodes 209A and 209B, that electrically link the right atrial lead 201 with the heart 220. Both the coronary sinus lead 200 and the right atrial lead 201 can be installed using either over-the-wire (referred to as "OTW") or non-OTW techniques, such as stylet driving or catheter delivering.

In the example shown in FIG. 2, the coronary sinus lead 200 is a quadripolar lead including a proximal electrode 208A, two intermediate electrodes 208B, 208C, and a distal electrode 208D. The right atrial lead 201 is a bipolar lead including a proximal electrode 209A and a distal electrode 209B. Each of the electrodes 208A, 208B, 208C, 208D, 209A, and 209B can, for example, comprise ring electrodes or single or multi-filar shock coil electrodes and are independently connected to a separate (corresponding) electrically conductive terminal within a header 210 of the CFM device 102. The header 210 is affixed to a hermetically sealed housing 212, which may be formed from a conductive metal such as titanium, and which carries the electronic circuitry of the CFM device 102. In this example, the header 210 includes a header electrode 214 and the housing 212 includes a housing electrode 216, both of which may be used in one or more electrode configurations for sensing or stimulating heart 108, as further described or incorporated in Hansen, et al., U.S. Patent Publication No. 2007/0066998 entitled "MULTI-SITE LEAD/SYSTEM USING A MULTI-POLE CONNECTION AND METHODS THEREFOR," assigned to the assignee of the present patent application, the disclosure of which is incorporated herein by reference in its entirety.

Figure 3:
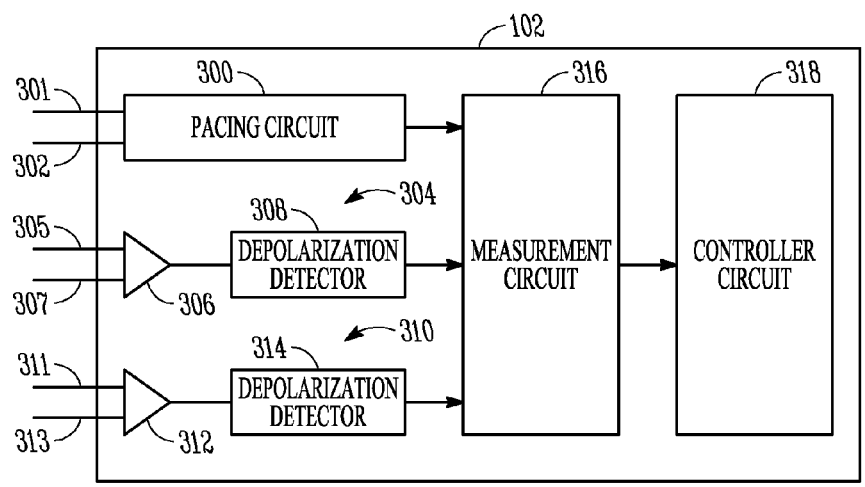
FIG. 3 is a block diagram illustrating generally an example of a cardiac function management device for identifying atrial sense and capture signals.

FIG. 3 is a block diagram illustrating generally an example of portions of a CFM device 102 that can be used to identify atrial sense or capture. The device 102 includes circuitry which receives one or more cardiac signals and delivers electrical energy to electrodes positioned within a subject's heart. The device 102 can include a pacing circuit 300 configured to be electrically coupled to a coronary sinus pacing electrode (not shown), such as via terminals 301 and 302. The coronary sinus pacing electrode can be configured to pace a first atrial chamber, such as the left atrial chamber, for example. The coronary sinus pacing electrode can be inserted via a subject's coronary sinus. In an example, the coronary sinus pacing electrode can be an electrode on a single electrode or multi-electrode (e.g., quadripolar) lead inserted via the coronary sinus. The coronary sinus pacing electrode can be located at or near the AV groove or in the left ventricular region. In an example, the coronary sinus pacing electrode can be used to detect left atrial depolarizations, left ventricular depolarizations, or both. In an example the coronary sinus pacing electrode can be configured to provide overdrive pacing, such that the pacing rate is faster than the intrinsic heart rate (e.g., at least 10 beats per minute higher than the intrinsic heart rate). In an example, the coronary sinus pacing electrode can be configured to provide pacing at a rate that is high enough to ensure capture when capture is possible.

The device 102 can include a first sensing circuit 304, which can be configured to sense an atrial depolarization associated with a second atrial chamber, such as the right atrial chamber, for example. The first sensing circuit 304 can include a sense amplifier 306 and a depolarization detector 308. The first sensing circuit 304 can be electrically coupled to terminals 305 and 307. These terminals, in turn, can be coupled to heart sites (e.g., in or near the right atrium) via intravascular endocardial leads, to allow for the one or more cardiac signals to be sensed in the heart.

In an example, the device 102 can further include a second sensing circuit 310, which can be configured to sense left atrial depolarizations, left ventricular depolarizations, or both. The second sensing circuit 310 can include a sense amplifier 312 and a depolarization detector 314. The second sensing circuit 310 can be electrically coupled to terminals 311 and 313. These terminals, in turn, can be coupled to heart sites (e.g., in or near the coronary sinus) via intravascular endocardial leads, to allow for the one or more cardiac signals to be sensed in the heart.

Additionally, device 102 can include a measurement circuit 316, which can be coupled to the pacing circuit 300 and the sensing circuits 304 and 310. The measurement circuit 316 can be configured to measure a parameter, such as a rate or a morphological feature, of the second atrial chamber depolarization. In an example, when the right atrial chamber depolarization is sensed in the absence of pacing from the coronary sinus pacing electrode, the measurement circuit 316 can be configured to perform a first measurement of a parameter of the right atrial chamber depolarization in the absence of pacing from the coronary sinus pacing electrode. The measurement circuit 316 can further be configured to perform a second measurement of the same parameter of the right atrial chamber depolarization in the presence of pacing from the coronary sinus pacing electrode, when the right atrial chamber depolarization is sensed in the presence of pacing from the coronary sinus pacing electrode.

Examples of parameters that can be measured by the measurement circuit 316 include heart rate, p-wave duration, p-wave vector direction, p-wave amplitude, p-wave slope, p-wave power, p-wave frequency content, p-wave area, and depolarization conduction time between the coronary sinus pacing electrode and an electrode associated with the second atrial chamber. In an example, the measurement circuit 316 can be configured to measure a combination of parameters. In an example, morphological features, such as p-wave duration, p-wave vector direction, p-wave amplitude, p-wave slope, and p-wave area, can be determined using a sensed electrocardiogram (ECG) signal indicative of a sensed cardiac depolarization. Template matching algorithms or other morphology-based analysis can be used to identify a morphological feature or a change in a morphological feature. In an example, p-wave vector direction can be determined by calculating one or more angles using trigonometric identities to indicate a vector's direction relative to other vectors in a coordinate system, such as described or incorporated in Zhang U.S. Pat. No. 7,567,836 entitled "ECG SIGNAL POWER VECTOR DETECTION OF ISCHEMIA OR INFARCTION," assigned to the assignee of the present patent application, the disclosure of which is incorporated herein by reference in its entirety.

The device 102 can include a controller circuit 318, which can be coupled to the measurement circuit 316. The controller circuit 318 can be configured to compare a change between the first and second measurements to a criterion. In an example, controller circuit 318 can be configured to compare a change between a central tendency of first measurements and a central tendency of second measurements to a criterion. In an example, the change between the first and second measurements can be a difference between a right atrial rate measured in the absence of pacing from the coronary sinus pacing electrode and a right atrial rate measured in the presence of pacing from the coronary sinus electrode. In this example, the criterion can be a specified number of beats per minute (bpm) (e.g., 5-10 bpm). The controller circuit 318 can be configured such that, when the change between the first and second measurements meets the criterion, the controller circuit can declare that the first atrial chamber (e.g. the left atrial chamber) has been captured by the pacing from the coronary sinus pacing electrode. Thus, in an example, if the right atrial rate measured in the absence of pacing from the coronary sinus pacing electrode is 60 bpm, and the right atrial rate measured in the presence of pacing from the coronary sinus pacing electrode is 90 bpm, and the criterion is 10 bpm, then the controller circuit 318 can be configured to declare that the left atrial chamber has been captured by the pacing from the coronary sinus pacing electrode.

In an example, the controller circuit 318 can be coupled to the pacing circuit 300 and can be configured to vary an energy of paces delivered by the coronary sinus pacing electrode to determine a first atrial chamber capture threshold energy associated with the coronary sinus pacing electrode. For example, in order to determine a first atrial chamber capture threshold energy associated with the coronary sinus pacing electrode, the controller circuit 318 can be configured to incrementally decrease or increase pacing energy until capture is either lost or obtained.

In an example, the device 102 can include a coronary sinus sensing electrode (not shown), which can be electrically coupled to the second sensing circuit 310. The coronary sinus sensing electrode can be configured to sense a cardiac depolarization, and it can be configured to be inserted via the coronary sinus. In an example, the coronary sinus sensing electrode and the coronary sinus pacing electrode are the same electrode. In an example, the measurement circuit 316 can be configured to measure a delay between the second atrial chamber (e.g. right atrial chamber) depolarization and the cardiac depolarization sensed at the coronary sinus sensing electrode during the same cardiac cycle. In this example, the controller circuit 318 can be configured to use information about the delay to determine whether the sensed cardiac depolarization is associated with the first atrial chamber (e.g. left atrial chamber). For example, the controller circuit 318 can be configured to compare the delay to a specified threshold value, and when the delay is less than the specified threshold value, to declare that the sensed cardiac depolarization is associated with the first atrial chamber (e.g. as opposed to being associated with the contralateral first ventricular chamber or any other cardiac chamber).

In an example, the device 102 can include multiple coronary sinus sensing electrodes located at different locations in the coronary sinus region. In this example, the measurement circuit 316 can be configured to measure delays between the second atrial chamber depolarization and the cardiac depolarization sensed at each of the coronary sinus sensing electrodes. The controller circuit 318 can be configured to compare the delays to determine whether the sensed cardiac depolarization is associated with the first atrial chamber. For example, if a shorter delay is measured using one sensing electrode, as compared to the delays measured using other sensing electrodes, the controller circuit 318 can be configured to determine that the sensed cardiac depolarization is associated with the first atrial chamber (e.g., as opposed to being associated with the contralateral first ventricular chamber or any other cardiac chamber).

Figure 4:
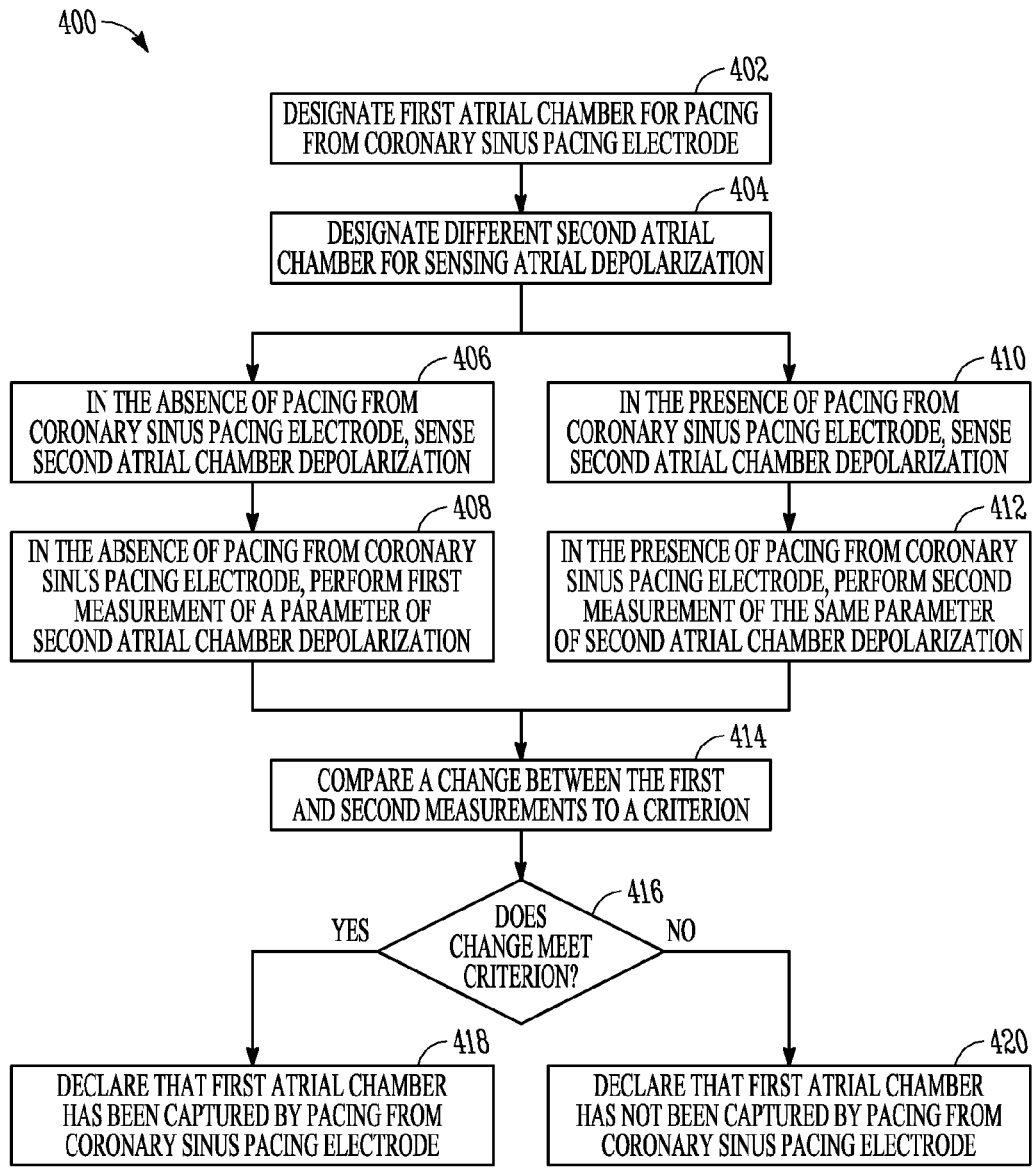
FIG. 4 is a chart illustrating generally an example of a method for determining whether an atrial chamber has been captured by pacing from a coronary sinus pacing electrode.

FIG. 4 is a chart illustrating generally an example of a method 400 for determining whether an atrial chamber has been captured by pacing from a coronary sinus pacing electrode. At 402, a first atrial chamber (e.g., left atrial chamber) is designated for pacing from a coronary sinus pacing electrode, which has been inserted via the coronary sinus of a subject's heart. At 404, a different second atrial chamber (e.g., right atrial chamber) is designated for sensing an atrial depolarization associated with the second atrial chamber. At 406, in the absence of pacing from the coronary sinus pacing electrode, a second atrial chamber depolarization is sensed. At 408, in the absence of pacing from the coronary sinus pacing electrode, a first measurement of a parameter (e.g., a heart rate or a morphological characteristic) of the second atrial chamber depolarization is performed. Examples of parameters that can be measured include heart rate, p-wave duration, p-wave vector direction, p-wave amplitude, p-wave slope, p-wave power, and p-wave frequency content, p-wave area, and depolarization conduction time between the coronary sinus pacing electrode and an electrode associated with the second atrial chamber, or any combination of the above. In an example, performing a first measurement of a parameter of the second atrial chamber depolarization in the absence of pacing from the coronary sinus pacing electrode can include measuring an intrinsic rate of right atrial depolarization.

At 410, in the presence of pacing from the coronary sinus pacing electrode, a second atrial depolarization is sensed. At 412, in the presence of pacing from the coronary sinus pacing electrode, a second measurement of the same parameter (e.g., the parameter performed during the first measurement at 408) of the second atrial chamber depolarization is performed. Thus, in an example, if the first measurement performed at 408 included measuring an intrinsic rate of right atrial depolarization, the second measurement performed at 412 can include measuring the rate of right atrial depolarization when the coronary sinus pacing electrode is providing overdrive pacing (e.g., 30 bpm above the intrinsic heart rate) in the coronary sinus region between the left atrium and the left ventricle.

At 414, a change between the first and second measurements is compared to a criterion. At 416, a determination is made as to whether the change meets the criterion. If the change meets the criterion, at 418, it is declared that the first atrial chamber has been captured by pacing from the coronary sinus pacing electrode. If the change does not meet the criterion, at 420, it is declared that the first atrial chamber has not been captured by pacing from the coronary sinus pacing electrode.

Continuing with the above example, the change between the intrinsic right atrial depolarization rate and the right atrial depolarization rate in the presence of overdrive pacing from the coronary sinus pacing electrode is compared to a criterion. In an example, the intrinsic right atrial depolarization rate is 60 bpm, the right atrial depolarization rate during overdrive pacing from the coronary sinus is 90 bpm, and the criterion is 10 bpm. In this example, the change between the two right atrial depolarization rates is greater than 10 bpm (90−60>10), the criterion has been met, and it can be declared that the left atrial chamber has been captured by pacing from the coronary sinus pacing electrode. In this example, it is believed that, because of the linked conduction system between the atria, the change in the rate of right atrial depolarization is due pacing of the left atrium (e.g., as opposed to the left ventricle) by the coronary sinus pacing electrode.

In an example, performing, at 408, the first measurement of a parameter of the second atrial chamber depolarization can include measuring the duration of an intrinsic right atrial p-wave sensed during a right atrial chamber depolarization. In this example, at 412, performing the second measurement can include measuring the duration of a right atrial p-wave sensed during a right atrial chamber depolarization in the presence of pacing from the coronary sinus pacing electrode. The pacing from the coronary sinus pacing electrode can include pacing with a specified AV delay, such as 30 milliseconds. In this example, the criterion can be a specified duration of time, such as 20 milliseconds. Thus, at 416, if a change between the intrinsic right atrial p-wave duration and the right atrial p-wave duration in the presence of a specified AV delay pacing from the coronary sinus pacing electrode is greater than 20 milliseconds, the criterion has been met, and it can be declared, at 418, that the left atrial chamber has been captured by pacing from the coronary sinus pacing electrode. In this example, it is believed that, because of the linked conduction system between the atria, the change in the duration of the right atrial p-wave is due pacing of the left atrium (e.g., as opposed to the left ventricle) by the coronary sinus pacing electrode.

In an example, when it is declared that the first atrial chamber has been captured by pacing from a particular coronary sinus pacing electrode, such as a first coronary sinus pacing electrode, the first coronary sinus pacing electrode can then be added to a list of candidate electrodes that can be useful for pacing the left atrium and removed from a list of candidate electrodes that can be useful for pacing the left ventricle. In an example, when it is declared that the first atrial chamber has not been captured by a particular coronary sinus pacing electrode, such a second coronary sinus pacing electrode, the second coronary sinus pacing electrode can be removed from a list of candidate electrodes that can be useful for pacing the left atrium and added to a list of candidate electrodes that can be useful for pacing the left ventricle. Once a list of candidate electrodes useful for pacing the left atrium has been compiled, it can be presented to a user or an automated process to select a left atrial pacing vector using an electrode selected from among the list of candidate electrodes. Likewise, once a list of candidate electrodes useful for pacing the left ventricle has been compiled, it can be presented to a user or an automated process to select a left ventricular pacing vector using an electrode selected from among the list of candidate electrodes. An automated process can be used to select a pacing vector such as by using any one or more of the existing automatic vector selection techniques. In an example, a threshold voltage can be used by either an automated process or a user to select a particular candidate electrode, from the list of candidate electrodes, to be used in a pacing vector. Pacing vector selection can further be performed as described in Sathaye et al. U.S. Patent Publication No. 2009/0043351 entitled "METHOD AND APPARATUS TO PERFORM ELECTRODE COMBINATION SELECTION," assigned to the assignee of the present patent application, the disclosure of which is incorporated herein by reference in its entirety.

Figure 5:
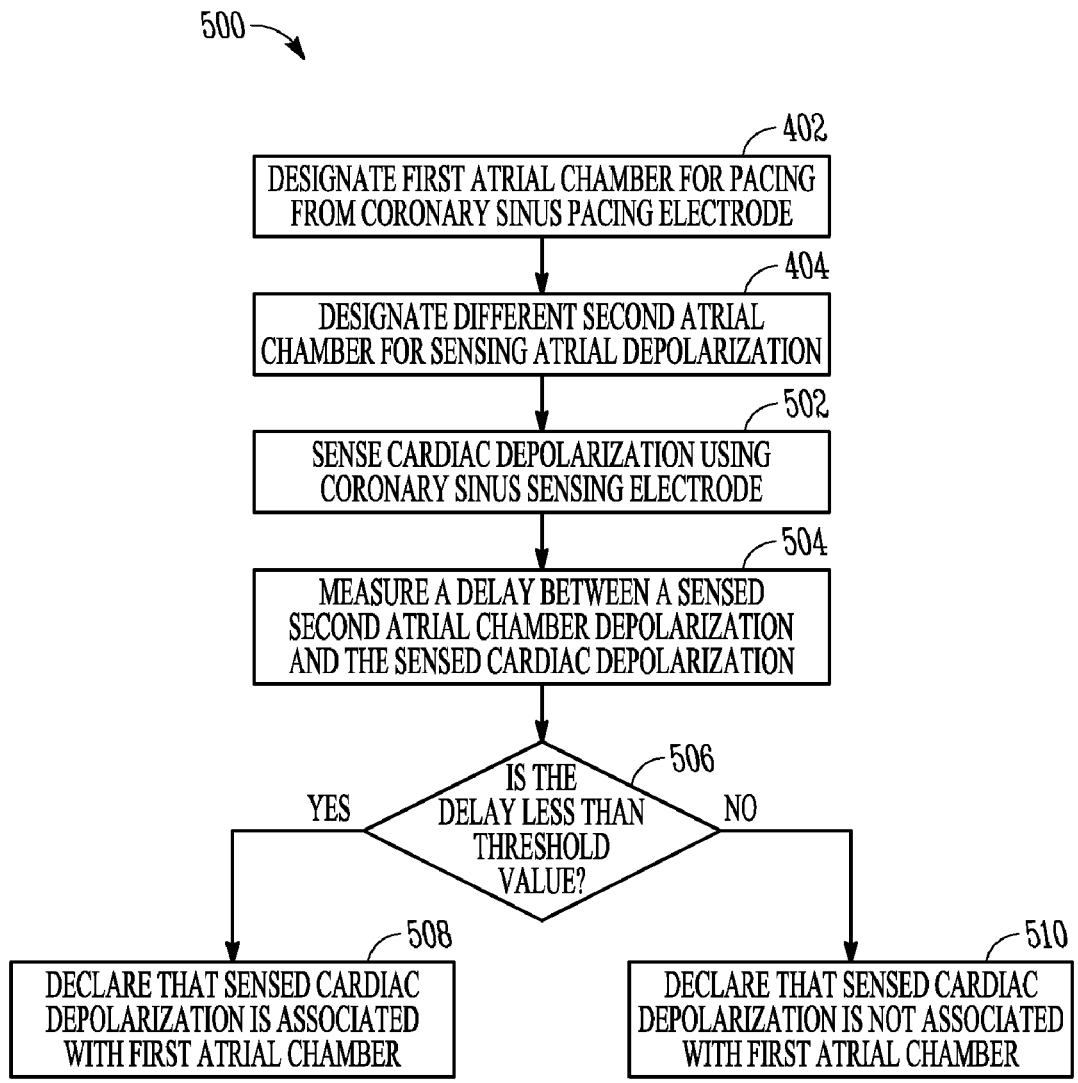
FIG. 5 is a chart illustrating generally an example of a method for determining whether a cardiac depolarization, sensed using a coronary sinus sensing electrode, is associated with an atrial chamber.

FIG. 5 is a chart illustrating generally an example of a method 500 for determining whether a cardiac depolarization, sensed using a coronary sinus sensing electrode, is associated with an atrial chamber. At 402, a first atrial chamber (e.g., left atrial chamber) is designated for pacing from a coronary sinus pacing electrode, which has been inserted via the coronary sinus of a subject's heart. At 404, a different second atrial chamber (e.g., right atrial chamber) is designated for sensing an atrial depolarization associated with the second atrial chamber. At 502, a cardiac depolarization is sensed using a coronary sinus sensing electrode that has been inserted via the coronary sinus of the subject's heart. In an example, the coronary sinus sensing electrode and the coronary sinus pacing electrode can be the same electrode. The sensed cardiac depolarization can be associated with one of the left atrium or the left ventricle, for example. At 504, a delay is measured between the sensed second atrial chamber depolarization and the cardiac depolarization sensed at the coronary sinus sensing electrode during the same cardiac cycle. At 506, a determination is made as to whether the delay is less than a specified threshold value. In an example, the specified threshold value can be an estimated maximal interatrial delay value. If the delay is less than the specified threshold value, at 508, it is declared that the sensed cardiac depolarization is associated with the first atrial chamber. If the delay is not less than the specified threshold value, at 510, it is declared that the sensed cardiac depolarization is not associated with the first atrial chamber.

In an example, at 504, a delay is measured between a sensed right atrial depolarization and the cardiac depolarization sensed at the coronary sinus sensing electrode during the same cardiac cycle. At 506, the delay is compared to a threshold value representing an estimated maximal interatrial delay, which, in an example, can be 100 milliseconds. In this example, if the delay is less than 100 milliseconds, then, at 508, it can be determined that the sensed cardiac depolarization is associated with the left atrial chamber. In this case, it is believed that because the delay between the sensed right atrial depolarization and the sensed cardiac depolarization is within the estimated maximal interatrial delay period, the sensed cardiac depolarization is being sensed from the other atrium (e.g., the left atrium). If the delay is greater than 100 milliseconds, then, at 510, it can be determined that the sensed cardiac depolarization is not associated with the left atrial chamber, and, instead, is likely associated with the left ventricular chamber. The delay in this case can represent the AV delay, which is longer than the interatrial delay.

In an example, when it is determined that the sensed cardiac depolarization is associated with the first atrial chamber, the particular coronary sinus sensing electrode that was used to sense the cardiac depolarization can then be added to a list of candidate electrodes that can be useful for sensing left atrial depolarizations and removed from a list of candidate electrodes that can be useful for sensing left ventricular depolarizations. In an example, when it is determined that the sensed cardiac depolarization is not associated with the first atrial chamber, the particular coronary sinus sensing electrode that was used to sense the cardiac depolarization can then be removed from a list of candidate electrodes that can be useful for sensing left atrial depolarizations and added to a list of candidate electrodes that can be useful for sensing left ventricular depolarizations. Once a list of candidate electrodes useful for sensing the left atrium has been compiled, it can be presented to a user or an automated process to select a left atrial sensing vector using an electrode selected from among the list of candidate electrodes. Likewise, once a list of candidate electrodes useful for sensing the left ventricle has been compiled, it can be presented to a user or an automated process to select a left ventricular sensing vector using an electrode selected from among the list of candidate electrodes. An automated process can be used to select a sensing vector such as by using any one or more of the existing automatic vector selection techniques. In an example, depolarization amplitude or timing can be used by either an automated process or a user to select a particular candidate electrode, from the list of candidate electrodes, to be used in a sensing vector.

Figure 6:
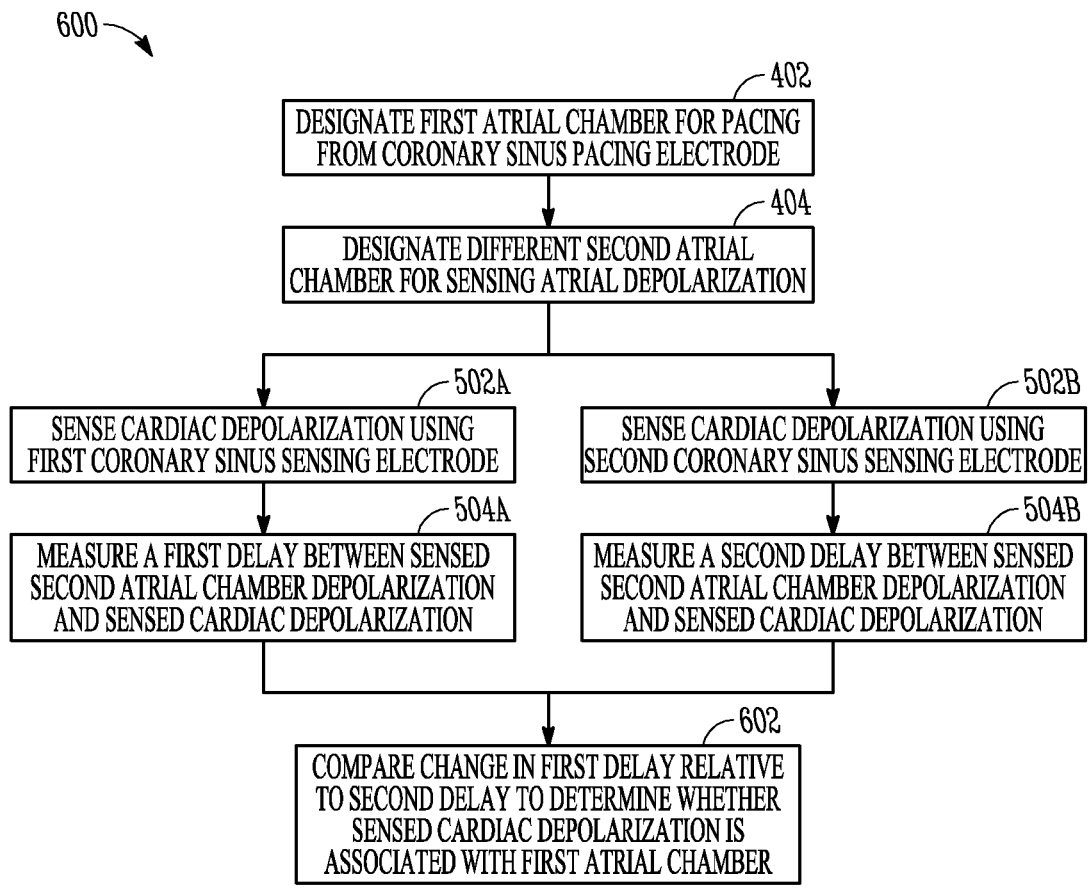
FIG. 6 is a chart illustrating generally an example of a method for determining whether a cardiac depolarization, sensed at multiple coronary sinus sensing electrodes, is associated with an atrial chamber.

FIG. 6 is a chart illustrating generally an example of a method 600 for determining whether a cardiac depolarization, sensed at multiple coronary sinus sensing electrodes, is associated with an atrial chamber. At 402, a first atrial chamber (e.g., left atrial chamber) is designated for pacing from a coronary sinus pacing electrode, which has been inserted via the coronary sinus of a subject's heart. At 404, a different second atrial chamber (e.g., right atrial chamber) is designated for sensing an atrial depolarization associated with the second atrial chamber. At 502A, a cardiac depolarization is sensed using a first coronary sinus sensing electrode. At 502B, the same cardiac depolarization is sensed using a second coronary sinus sensing electrode that is located at a different coronary sinus location than the first coronary sinus sensing electrode. At 504A, a first delay is measured between the sensed second atrial chamber depolarization and the cardiac depolarization sensed at the first coronary sinus sensing electrode during the same cardiac cycle. At 504B, a second delay is measured between the sensed second atrial chamber depolarization and the cardiac depolarization sensed at the second coronary sinus sensing electrode during the same cardiac cycle. At 602, a comparison is made between the first delay and the second delay, and, based on a change in the first delay relative to the second delay, a determination is made as to whether the sensed cardiac depolarization is associated with the first atrial chamber.

Figure 7:
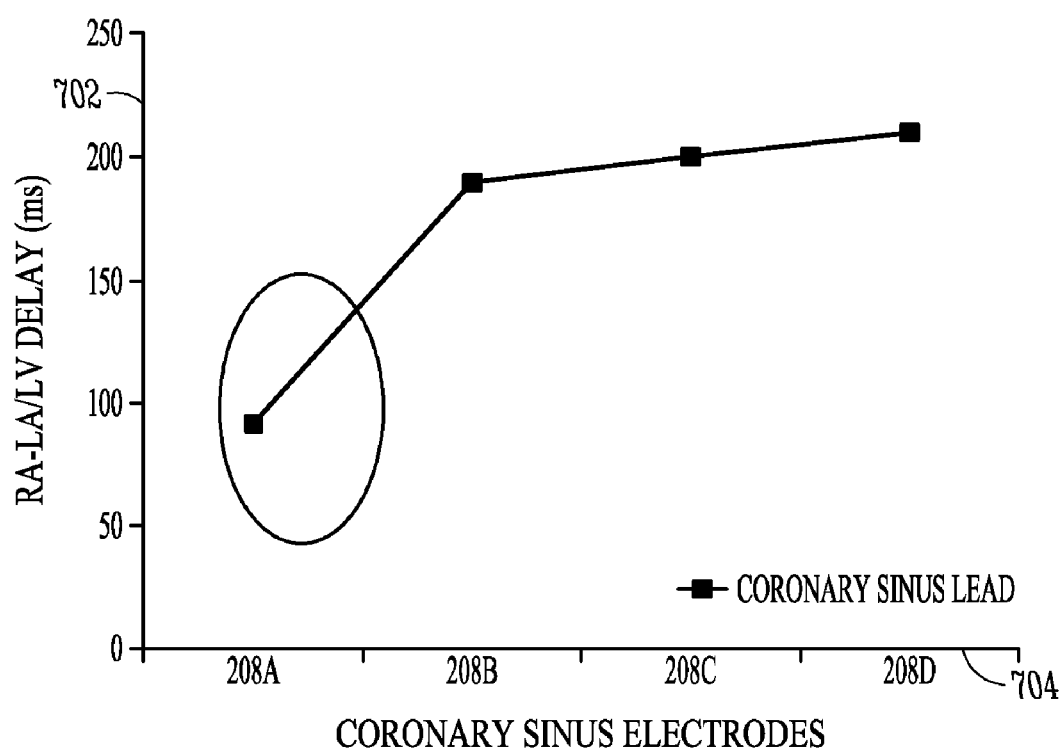
FIG. 7 is a diagram illustrating generally an example of conceptual data that can be obtained using a method for determining whether a cardiac depolarization, sensed at multiple coronary sinus sensing electrodes, is associated with an atrial chamber.

The method 600 described above with respect to FIG. 6 can be further described with respect to FIG. 7, a diagram illustrating generally an example of conceptual data that can be obtained using method 600. The diagram in FIG. 7 illustrates a delay between a sensed right atrial (RA) depolarization and a cardiac depolarization, sensed at four different coronary sinus sensing electrodes, representing either a left atrial (LA) depolarization or a left ventricular (LV) depolarization. Whether the sensed cardiac depolarization is represents a sensed LA depolarization or a sensed LV depolarization can depend on the position of the coronary sinus sensing electrode. The RA-LA/LV delay, measured in milliseconds (ms), is represented along the Y-axis 702. The RA-LA/LV delay is measured using a RA sensing electrode (not shown) and one of four different coronary sinus sensing electrodes, which are represented along the X-axis 704. In this example, electrodes 208A, 208B, 208C, and 208D are located on a quadripolar coronary sinus lead (see FIG. 2). Each coronary sinus electrode can be located at a different location associated with the coronary sinus.

In this example, the delay is measured between the RA depolarization and the cardiac depolarization sensed at coronary sinus electrode 208D is about 210 ms. The delay measured between the RA depolarization and the cardiac depolarization sensed at coronary sinus electrode 208C is about 200 ms. The delay measured at between the RA depolarization and the cardiac depolarization sensed at coronary sinus electrode 208B is about 190 ms. The delays measured at electrodes 208D, 208C, and 208B fall within a normal range for an atrioventricular delay. Thus, it can be assumed that the cardiac depolarization sensed at electrodes 208D, 208C, and 208B are left ventricular depolarizations. However, the delay measured between the RA depolarization and the cardiac depolarization sensed at coronary sinus electrode 208A is much shorter than the delays measured at the other three coronary sinus electrodes. The delay measured using electrode 208A is about 90 ms. This shortened delay can suggest that electrode 208A is sensing a left atrial contraction, and, therefore, the delay measured between the RA depolarization and the cardiac depolarization sensed at coronary sinus electrode 208A is an interatrial delay.

In an example, when a RA-LA/LV delay is measured using multiple coronary sinus electrodes at different locations within the coronary sinus, a delay measured at one electrode, such as 208A, can be compared to the delays measured at adjacent electrodes (e.g., 208B, 208C, and 208D). If there is a change in the delay measured using electrode 208A compared to the delays measured at the adjacent electrodes, and the change is greater than a specified threshold (e.g., 20 ms), then left atrial sensing at can be declared.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A cardiac function management device comprising:
    a pacing circuit comprising a coronary sinus pacing electrode configured to be inserted via a coronary sinus of a heart of a subject, the coronary sinus pacing electrode configured to pace a first atrial chamber;
    a sensing circuit configured to sense an atrial depolarization associated with a different second atrial chamber;
    a measurement circuit, coupled to the pacing circuit and the sensing circuit, the measurement circuit configured to:
        perform a first measurement of a parameter of the second atrial chamber depolarization in the absence of pacing from the coronary sinus pacing electrode, wherein the second atrial chamber depolarization is sensed in the absence of pacing from the coronary sinus pacing electrode; and
        perform a second measurement of the same parameter of the second atrial chamber depolarization in the presence of pacing from the coronary sinus pacing electrode, wherein the second atrial chamber depolarization is sensed in the presence of pacing from the coronary sinus pacing electrode; and
    a controller circuit, coupled to the measurement circuit, the controller circuit configured to compare a change between the first and second measurements to a criterion, and when the change meets the criterion, to declare that the first atrial chamber has been captured by the pacing from the coronary sinus pacing electrode.

2. The device of claim 1, wherein the change between the first and second measurements comprises an increase in heart rate.

3. The device of claim 1, wherein the change between the first and second measurements comprises a change in a cardiac depolarization morphology characteristic.

4. The device of claim 1, wherein the change between the first and second measurements comprises a change in at least one of: a P-wave duration, a P-wave vector direction, a P-wave amplitude, a P-wave slope, a P-wave power, a P-wave frequency content, a P-wave area, a P-wave morphological feature, a P-wave spatiotemporal characteristic, or a change in depolarization conduction time between the coronary sinus pacing electrode and an electrode associated with the second atrial chamber.

5. The device of claim 1, wherein the controller circuit is coupled to the pacing circuit and configured to vary an energy of paces delivered by the coronary sinus pacing electrode to determine a first atrial chamber capture threshold energy associated with the coronary sinus pacing electrode.

6. The device of claim 1, wherein the change between the first and second measurements comprises a change in heart rate and a change in a depolarization morphology characteristic.

7. The device of claim 1, comprising a coronary sinus sensing electrode, configured to be inserted via a coronary sinus of the heart of the subject, the coronary sinus sensing electrode configured to sense a cardiac depolarization;
    wherein the measurement circuit is configured to measure a delay between the sensed second atrial chamber depolarization and the sensed cardiac depolarization sensed at the coronary sinus sensing electrode during the same cardiac cycle; and wherein the controller circuit is configured to use information about the delay to determine whether the sensed cardiac depolarization is associated with the first atrial chamber.

8. The device of claim 7, wherein the coronary sinus sensing electrode and the coronary sinus pacing electrode are the same electrode.

9. The device of claim 7, wherein the controller circuit is configured to compare the delay to a specified threshold value, and when the delay is less than the specified threshold value, to declare that the sensed cardiac depolarization is associated with the first atrial chamber.

10. The device of claim 7, wherein the coronary sinus sensing electrode comprises first and second coronary sinus sensing electrodes located at different coronary sinus locations;

wherein the measurement circuit is configured to:
measure a first delay between the sensed second atrial chamber depolarization and the sensed cardiac depolarization sensed at the first coronary sinus sensing electrode during the same cardiac cycle; and
measure a second delay between the sensed second atrial chamber depolarization and the sensed cardiac depolarization sensed at the second coronary sinus sensing electrode during the same cardiac cycle; and
wherein the controller is configured to compare a change in the first delay relative to the second delay to determine whether the sensed cardiac depolarization is associated with the first atrial chamber.

11. A method comprising:
designating a first atrial chamber for pacing from a coronary sinus pacing electrode that has been inserted via a coronary sinus of a heart of a subject;
designating a different second atrial chamber for sensing an atrial depolarization associated with the second atrial chamber;
sensing a second atrial chamber depolarization in the absence of pacing from the coronary sinus pacing electrode, and performing a first measurement of a parameter of the second atrial chamber depolarization in the absence of pacing from the coronary sinus pacing electrode;
sensing the second atrial chamber depolarization in the presence of pacing from the coronary sinus pacing electrode, and performing a second measurement of the same parameter of the second atrial chamber depolarization in the presence of pacing from the coronary sinus pacing electrode; and
comparing a change between the first and second measurements to a criterion, and when the change meets the criterion, declaring that the first atrial chamber has been captured by the pacing from the coronary sinus pacing electrode.

12. The method of claim 11, wherein the change between the first and second measurements comprises an increase in heart rate.

13. The method of claim 11, wherein the change between the first and second measurements comprises a change in a cardiac depolarization morphology characteristic.

14. The method of claim 11, wherein the change between the first and second measurements comprises a change in at least one of: a P-wave duration, a P-wave vector direction, a P-wave amplitude, a P-wave slope, a P-wave power, or a P-wave frequency content, a P-wave area, a P-wave morphological feature, a P-wave spatiotemporal characteristic, or a change in depolarization conduction time between the coronary sinus pacing electrode and an electrode associated with the second atrial chamber.

15. The method of claim 11, comprising varying an energy of paces delivered by the coronary sinus pacing electrode to determine a first atrial chamber capture threshold energy associated with the coronary sinus pacing electrode.

16. The method of claim 11, wherein the change between the first and second measurements comprises a change in heart rate and a change in a depolarization morphology characteristic.

17. The method of claim 11, comprising:
sensing a cardiac depolarization using a coronary sinus sensing electrode that has been inserted via a coronary sinus of the heart of the subject;
measuring a delay between the sensed second atrial chamber depolarization and the sensed cardiac depolarization sensed at the coronary sinus sensing electrode during the same cardiac cycle; and
using information about the delay to determine whether the sensed cardiac depolarization is associated with the first atrial chamber.

18. The method of claim 17, wherein the coronary sinus sensing electrode and the coronary sinus pacing electrode are the same electrode.

19. The method of claim 17, wherein using information about the delay includes comparing the delay to a specified threshold value, and when the delay is less than the specified threshold value, declaring that the sensed cardiac depolarization is associated with the first atrial chamber.

20. The method of claim 17, wherein sensing a cardiac depolarization using a coronary sinus electrode includes using first and second coronary sinus sensing electrodes located at different coronary sinus locations;

wherein measuring a delay includes:
measuring a first delay between the sensed second atrial chamber depolarization and the sensed cardiac depolarization sensed at the first coronary sinus sensing electrode during the same cardiac cycle; and
measuring a second delay between the sensed second atrial chamber depolarization and the sensed cardiac depolarization sensed at the second coronary sinus sensing electrode during the same cardiac cycle; and
wherein using information about the delay includes comparing a change in the first delay relative to the second delay to determine whether the sensed cardiac depolarization is associated with the first atrial chamber.

* * * * *